United States Patent
Fusi et al.

(10) Patent No.: US 10,923,213 B2
(45) Date of Patent: Feb. 16, 2021

(54) LATENT SPACE HARMONIZATION FOR PREDICTIVE MODELING

(71) Applicant: Microsoft Technology Licensing, LLC, Redmond, WA (US)

(72) Inventors: Nicolo Fusi, Boston, MA (US); Jennifer Listgarten, Cambridge, MA (US); Gregory Byer Darnell, Princeton, NJ (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 811 days.

(21) Appl. No.: 15/367,729

(22) Filed: Dec. 2, 2016

(65) Prior Publication Data

US 2018/0157794 A1    Jun. 7, 2018

(51) Int. Cl.
| | |
|---|---|
| *G16B 40/00* | (2019.01) |
| *G06N 7/00* | (2006.01) |
| *G16B 40/20* | (2019.01) |
| *G06N 20/00* | (2019.01) |

(52) U.S. Cl.
CPC ............. *G16B 40/00* (2019.02); *G06N 7/005* (2013.01); *G06N 20/00* (2019.01); *G16B 40/20* (2019.02)

(58) Field of Classification Search
None
See application file for complete search history.

(56) References Cited

U.S. PATENT DOCUMENTS

| | | |
|---|---|---|
| 9,019,278 B2 | 4/2015 | Hodgins et al. |
| 2010/0179930 A1 | 7/2010 | Teller et al. |
| 2014/0095426 A1 | 4/2014 | Nicholson et al. |
| 2015/0095490 A1 | 4/2015 | Ning et al. |
| 2016/0048766 A1 | 2/2016 | McMahon et al. |

OTHER PUBLICATIONS

Sonnenburg et al. Large Scale Multiple Kernel Learning Journal of Machine Learning Research vol. 7, pp. 1531-1565 (Year: 2006).*
Soguero-Ruiz et al. Predicting colorectal surgical complications using heterogeneous clinical data and kernel methods Journal of Biomedical Informatics vol. 61, pp. 87-96 (Year: 2016).*
Lancriet et al. A statistical framework for genomic data fusion Bioinformatics vol. 20, pp. 2626-2635 (Year: 2004).*
Cristianini et al. Support Vector Machines and Kernel Methods the New Generation of Learning Machines AI Magazine vol. 23 pp. 31-41 (Year: 2002).*
Wang et al. Heterogeneous Cross Domain Ranking in Latent Space (CIKM '09 Proceedings of the 18th ACM Conference on Information and Knowledge Management pp. 987-995 (Year: 2009).*
Ganzert et al. Analysis of respiratory pressure-voume curves in intensive care medicine using inductive machine learning Artificial Intelligence in Medicine vol. 26, pp. 69-86 (Year: 2002).*
Ding, et al., "Low-Rank Common Subspace for Multi-view Learning", In Proceedings of IEEE International Conference on Data Mining, Dec. 14, 2014, pp. 110-119.
Wang, et al., "Heterogeneous Domain Adaptation Using Manifold Alignment", In Proceedings of the Twenty-Second International Joint Conference on Artificial Intelligence, Jul. 16, 2011, pp. 15-41-15-1546.
Wang, et al., "Heterogeneous Cross Domain Ranking in Latent Space", In Proceedings of the 18th ACM conference on Information and knowledge management, Nov. 2, 2009, 10 pages.
Snoek, et al., "Input Warping for Bayesian Optimization of Non-Stationary Functions", In Proceedings of the 31th International Conference on Machine Learning, Jun. 21, 2014, pp. 1-11.
Young, et al., "Accurate multimodal probabilistic prediction of conversion to Alzheimer's disease in patients with mild cognitive impairment", In Journal of NeuroImage: Clinical, vol. 2, May 19, 2013, pp. 735-745.
Zhang, et al., "Multi-Task Warped Gaussian Process for Personalized Age Estimation", In Proceedings of the Twenty-Third IEEE Conference on Computer Vision and Pattern Recognition, Jun. 13, 2010, pp. 2622-2629.
Ray, et al., "Bayesian Joint Analysis of Heterogeneous Data", In Journal of Bioinformatics, vol. 30, No. 10, May 2014, pp. 1-45.
Snelson, et al., "Warped Gaussian Processes", In Journal of Advances in neural information processing systems, vol. 16, Jun. 2004, 8 pages.
Fusi, et al., "Warped linear mixed models for the genetic analysis of transformed phenotypes", In Journal of Nature Communications, vol. 5, Sep. 19, 2014, pp. 1-8.
Pal, et al., "Probability Models for High Dynamic Range Imaging", In Proceedings of IEEE Computer Society Conference on Computer Vision and Pattern Recognition, Jun. 27, 2004, 8 pages.

* cited by examiner

*Primary Examiner* — John S Brusca
(74) *Attorney, Agent, or Firm* — Schwegman Lundberg & Woessner, P.A.

(57) ABSTRACT

In embodiments of latent space harmonization (LSH) for predictive modeling, different training data sets are obtained from different measurement methods, where input data among the training data sets is quantifiable in a common space but a mapping between output data among the training data sets is unknown. A LSH module receives the training data sets and maps a common supervised target variable of the output data to a shared latent space where the output data can be jointly yielded. Mappings from the shared latent space back to the output training data of each training data set are determined and used to generate a trained predictive model. The trained predictive model is useable to predict output data from new input data with improved predictive power from the training data obtained using various, otherwise incongruent, measurement techniques.

15 Claims, 4 Drawing Sheets

LATENT SPACE HARMONIZATION FOR PREDICTIVE MODELING

BACKGROUND

In computing environments, machine learning is often used in order to predict an output based on an input using knowledge or intelligence garnered from training. For example, machine learning can be used to predict the height of a child based on heights of the child's parents. In this example, a predictive model for the child's height can be trained using height measurements of fully-grown children, and corresponding height measurements of their respective parents. Using these known height measurements, a relationship between parents' height and their child's height can be inferred and used in a predictive model to estimate the future height of a child based only on knowledge of the parents' heights. However, conventional approaches to predictive modeling encounter problems when the data used to train the predictive model is obtained using different measurement techniques.

Continuing the example of predicting a child's height, conventional predictive models are unable to handle training data that includes some height measurements in inches and other height measurements of centimeters, without prior knowledge of a relationship between the different measurements, such as first converting the height measurements to a common unit. Thus, conventional predictive models encounter problems when data obtained from different measurement techniques is used to train the model without any indication that the training data is represented in different measurement scales. These problems are further compounded when dealing with training data that is measured using fundamentally different technologies where the training data cannot be converted to a common unit of measurement. As such, conventional predictive modeling techniques are limited to considering smaller sample sizes of data obtained using a common measurement technique. Because the accuracy of a predictive model improves as a sample size of the training data increases, conventional techniques are unable to train an effective predictive model when dealing with training data that is measured using fundamentally different technologies.

SUMMARY

This Summary introduces features and concepts of latent space harmonization for predictive modeling, which is further described below in the Detailed Description and/or shown in the Figures. This Summary should not be considered to describe essential features of the claimed subject matter, nor used to determine or limit the scope of the claimed subject matter.

Latent space harmonization for predictive modeling is described. In embodiments, a predictive model is trained on training data that was obtained using fundamentally different measurement techniques, such that the data obtained from a measurement technique is not generally comparable to or congruent with data obtained from another measurement technique. A computing system maintains different sets of training data for training the predictive model, which is useable to generate a predicted output based on input data, regardless of a measurement technique that would otherwise be needed to measure output values based on the input data. Each training data set includes one or more pairs of input values, as well as output values that were generated from the input values, as observed using a measurement technique. The output values in each training data set include a supervised target variable, which refers to a quantifiable value in an output measurement space obtained from observing a physical principle or phenomenon.

In order to train a predictive model using training data sets that include data represented among disparate and incomparable units of measurement, the techniques described herein harmonize input training data and associated supervised target variables of different training data sets to a shared latent space. The shared latent space yields a single coherent data set that can be mapped to supervised target variables obtained using fundamentally different measurement technologies. In implementations, the supervised target variables are mapped to the shared latent space using a monotonic class of transformations, which preserves a rank order for data within each respective training data set. Mapping functions for data obtained from each different measurement technology to the shared latent space represent a mathematical inference of how data in the shared latent space correlates to data spaces of the different measurement techniques. From this shared latent space, training data is jointly yielded and analyzed to generate and train a predictive model. The predictive model is then useable to generate predicted outputs from new input data, thereby mitigating the need to perform expensive testing on the new input data.

BRIEF DESCRIPTION OF THE DRAWINGS

Embodiments of latent space harmonization for predictive modeling are described with reference to the following Figures. Entities represented in the figures may be indicative of one or more entities and thus reference may be made interchangeably to single or plural forms of the entities in the discussion. The same numbers may be used throughout to reference like features and components that are shown in the Figures.

DETAILED DESCRIPTION

Figure 1:
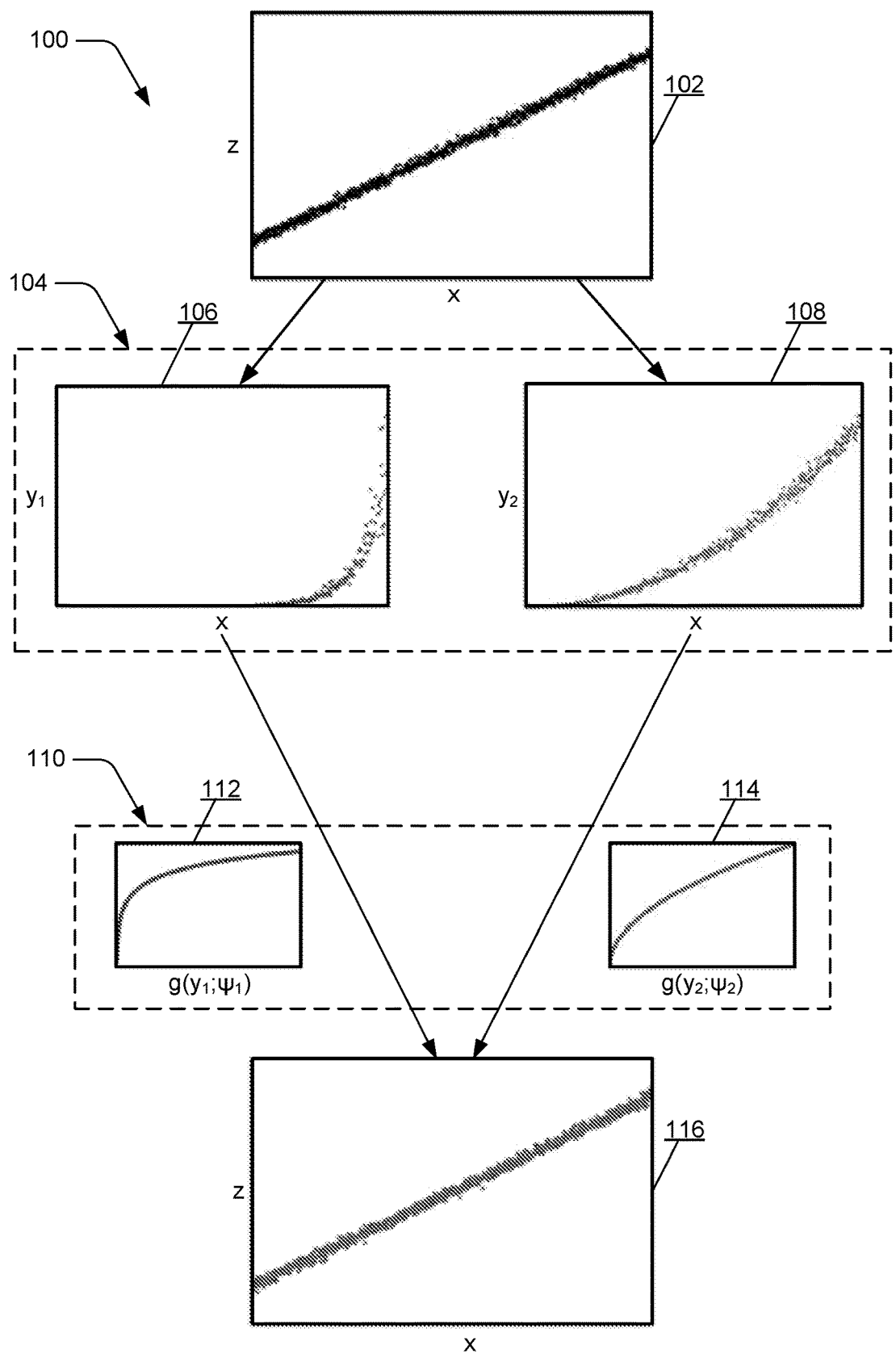
FIG. 1 illustrates an example of latent space harmonization for predictive modeling in accordance with one or more embodiments.

Embodiments of latent space harmonization are described for generating a predictive model from training data that was obtained using different measurement techniques, such that the predictive model can be used to generate a predicted output based on input data, regardless of the measurement technique that was used to obtain the input data. In implementations, different sets of training data are measured using fundamentally different techniques, such that a first set of training data is not comparable to a second set of training data, even if the first and second training data sets measure the same underlying physical principle or phenomenon. Accuracy of a predictive model is dependent on an amount of available training data, thus it is advantageous to train a predictive model using larger amounts of training data. As described herein, a "training data set" refers to a one or more pairs of input values and output values generated from the input values. The output values of a training data set include a "supervised target variable" for the training data, which refers to a quantifiable value in an output space that is obtained from measuring a physical principle or phenomenon using input data.

In many implementations, it is difficult to obtain large sample sizes of training data due to the cost associated with training data. For example, measurements pertaining to the human genome and related quantities such as gene function often require specialized equipment and procedures that are designed to perform only a narrow scope of measurements. For instance, various measurement techniques are used in evaluating gene knock out, in which a determination is made as to whether functionality of a particular gene in the human genome will be disabled, or "knocked out", in response to a particular attempt at cutting deoxyribonucleic acid (DNA) in that gene. Determining whether functionality of a particular gene is knocked out is performed using specialized lab equipment and processes. This determination is further complicated by the fact that different approaches must be used to analyze different classes of genes.

For example, determining gene knock out for the class of cell surface marker genes is performed using a flow cytometry process, while determining gene knock out for a different class of genes is performed by a drug resistance assay process. The resulting measurements from flow cytometry and drug resistance assay measurement techniques are output in different scales, with no knowledge of how measurements from the different techniques relate to one another. However, although there is no knowledge of how the results from the different measurement techniques relate to one another, some underlying mapping can be assumed between the measurements because the different techniques are directed at measuring a common supervised target variable. Although quantifiable on different measurement scales, the true (or latent) supervised target variable is independent of a measurement technique used to measure a physical principle or phenomenon, and thus can be used to connect different measurement techniques of a single physical principle or phenomenon.

For instance, in the gene knock out problem, the supervised target variable measured by both the flow cytometry and drug resistance assay techniques is an approximate probability that functionality of a particular gene in the human genome is disabled or knocked out. This supervised target variable is measured as part of output data and correlated with input data that was used to produce the output data. Continuing the gene knock out example, the probability that functionality of a particular gene is disabled is determined based on input data such as a certain 30-letter DNA sequence. The input data, output data, and the supervised target variable of the output data can then be combined into a training data set that is useable to train a predictive model for machine learning. This trained predictive model can then be used to predict outputs based on new input data, thereby saving substantial cost otherwise associated with testing the new input data in a laboratory to measure output values.

In developing a predictive model for use with machine learning, because there is no way to correlate measurement results that are obtained using fundamentally different measurement techniques, conventional predictive models are restricted to using training data sets that are generated using a single measurement technique. For example, in the gene knock out problem, conventional predictive models are limited to considering training data obtained using either flow cytometry or drug resistance assay techniques, and are unable to consider data obtained from both measurement techniques.

In order to account for different training data sets that measure a common supervised target variable using different measurement approaches and technologies, the techniques described herein harmonize supervised target variables of two or more different data sets to a shared latent space. As described herein, a shared latent space yields a single coherent data set that can be mapped to supervised target variables that were measured using fundamentally different measurement techniques. In accordance with one or more implementations, supervised target variables obtained using different measurement techniques are mapped to a shared latent space using a monotonic class of transformations, which refers to transformations between ordered sets of data that preserves or reverses a given order of the data. Thus, the shared latent space can be used to infer how data in the shared latent space maps back to data spaces of different measurement techniques that were used to obtain the common supervised target variable associated with the shared latent space. From this shared latent space, a predictive model can be learned by inferring the mappings of training data sets to the shared latent space, which yields a larger sample size used to train the predictive model, and therefore provides improved performance in predictive modeling. A trained predictive model can then be used to predict outputs from new input data instead of analyzing the new input data to obtain outputs with expensive and complicated measurement techniques.

While features and concepts of predictive modeling using latent space harmonization can be implemented in any number of different devices, systems, networks, environments, and/or configurations, embodiments of latent space harmonization for predictive modeling are described in the context of the following example devices, systems, and methods.

FIG. 1 illustrates an example system 100 in which measures of an underlying physical principle or phenomenon 102 can be mapped to a shared latent space. Generally, a shared latent space refers to a single coherent data set that can be mapped to two or more supervised target variables that were measured using fundamentally different measurement techniques. As described herein, a supervised target variable is a quantifiable value in an output space that is obtained from measuring a physical principle or phenomenon using input data. In aspects of latent space harmonization for predictive modeling, measures of an underlying physical principle or phenomenon 102 are represented by a scatter plot. This scatter plot of an underlying physical principle or phenomenon 102 represents a theoretical illustration of how input data 'x' corresponds to output data 'z' (i.e., on a respective x-axis and z-axis).

This illustration is theoretical in that it represents an unobserved correlation between input data and output data for measurements of a physical principle or phenomenon. The underlying physical principle or phenomenon 102 illustrated by the scatterplot in FIG. 1 is representative of any relationship between input data that is predictive of output data, such as parents' height used to predict a child's height, a DNA sequence used to predict knock out efficiency of a gene, a messenger ribonucleic acid (mRNA) sequence used to predict protein abundance, and so on. For example, an underlying physical phenomenon 102 pertaining to gene knock out would represent the DNA sequence applied to a gene as input data on the 'x' axis and the corresponding output of a probability that the gene was disabled is represented as output data on the 'z' axis.

In order to model a physical principle or phenomenon, measurements are taken to determine actual output data that is generated from actual input data. Examples of measurements taken from the underlying physical phenomenon 102 illustrated in FIG. 1 are represented by measurement groups 104, which include a first measurement group 106 and a second measurement group 108. Although only illustrated as including two measurement groups, measurement groups 104 may include any suitable number of measurement groups. Individual ones of the measurement groups 104 represent measurements of input and output data corresponding to the underling physical principle or phenomenon 102. For example, in the context of a gene knock out problem, the first measurement group 106 may represent input and output data measured on cell surface marker genes using flow cytometry measurement techniques. Likewise, the second measurement group 108 may represent input and output data measured on drug resistance genes using drug resistance assay measurement techniques.

Continuing this example, values on the 'x' axes of the measurement groups 104 represent input data used to measure gene knock out efficiency, such as a DNA string. Values on the 'y' axes of the measurement groups 104 represent output data that is observed from corresponding input data, such as the efficiency of an input data value in knocking out a particular gene. Input and output data of the different measurement groups 104 are grouped according to the measurement technique that was used to observe an underlying physical principle or phenomenon. Thus, the output data represented on the '$y_1$' axis of measurement group 106 represents output data measured according to a first method of measurement, while the output data represented on the '$y_2$' axis of measurement group 108 represents output data measured according to a second method of measurement.

Due to the output data being measured on different scales based on a method of measurement used to obtain the output data, there may not be a known approach to correlating the output data among different measurement groups 104. However, because the input data for each of the measurement groups 104 shares a common measurement scale and because the output data for each of the measurement groups 104 is directed to a common supervised target variable, mapping the output data of measurement groups 104 to a shared latent space enables inference of a mathematical relationship between inputs and outputs across all measurement groups 104 that is representative of the underlying physical principle or phenomenon 102, as illustrated in the scatter plot.

As described herein, a shared latent space refers to a single coherent data set that can be mapped to supervised target variables that were measured using fundamentally different measurement techniques. In accordance with one or more implementations, supervised target variables of the output data obtained using different measurement techniques are mapped to a shared latent space using a monotonic class of transformations, which refers to transformations between ordered sets of data that preserves or reverses a given order of the data.

In order to map the output data of the measurement groups 104 to a shared latent space, the techniques described herein apply mapping functions 110 to the output data of the measurement groups 104. Because output data of measurement groups 106 and 108 is assumed to be represented on its own measurement scale, individual mapping functions are used for different measurement groups used to measure data of an underlying physical principle or phenomenon. For example, mapping function 112 is used to map output data of measurement group 106 to the shared latent space 116. Similarly, mapping function 114 is used to map output data of measurement group 108 to the shared latent space 116. Although the mapping functions 112 and 114 are not identical, the mapping functions 110 represent a potentially non-linear, monotonic mapping from output data of the measurement groups 104 to the shared latent space 116.

After supervised target variables in the output values of each measurement group 104 for a physical principle or phenomenon are mapped to the shared latent space 116, the mappings for each measurement group are used to generate a trained predictive model that is designed to generate predicted outputs from new input data, using principles of machine learning. Thus, the techniques described herein unify disparate measurement spaces for a common supervised target variable into a shared latent space and generate predicted outputs from new input data using the trained predictive model that is trained based on data across disparate measurement spaces.

For example, the measurement groups 104 may include input data and output data that can be represented as $N_m$ pairs of input and output measurements of an underlying physical principle or phenomenon. In this example, input data is represented as $x_n^m$ and output data is represented as $y_n^m$ for M groups, and the input data is paired with output data ($x_n^m, y_n^m$). Each M group represents a different measurement technique used to observe a common underlying physical principle or phenomenon. Accordingly, it can be assumed that there exists a monotonic mapping for output data of each $y_n^m$ to output data in a shared latent space, represented on the 'z' axis of the shared latent space 116, as illustrated in FIG. 1.

The mapping of output data for each $y_n^m$ to the shared latent space 116 is assumed as represented in Equation (1):

$$y_n^m = g^{-1}(z_n; \psi_m)$$

such that the mapping of each measurement group of measurement groups 104 can be mapped to the shared latent space 116 using the function $g(y_m; \psi_m)$ for M measurement groups.

Every measurement pair of input data and output data for a single measurement group can be mathematically stated as ($X^m, y^m$), where $X^m$ includes all input data for a given measurement technique m, and $y^m$ includes all output data for a given measurement technique m. In order to train a predictive model for mapping all input values of a single measurement technique $x_n$ to output values in a shared latent space, represented as $z_n$, the techniques described herein use all available data from m different measurement techniques to simultaneously train the predictive model.

In order to generate such a trained predictive model, mappings $\psi_m$ from output data of different measurement techniques to a shared latent space are inferred, along with parameters "θ" for the predictive model. In an implementation, this predictive model may be a probabilistic model represented as $p(z_n | x_n^m, \theta)$, where θ represents a vector of parameters of the predictive model. For example, in one or more implementations, θ represents a fixed effects and noise parameter in a linear regression model. As discussed herein, this predictive model enables mapping new input data to unmeasured output data for a given physical principle or phenomenon, independent of a measurement technique that was used to measure the new input data.

Because the only available data available for training a predictive model is data obtained from the measurement groups 104, mathematically stated as $(X^m, y^m)$, estimating output data from new input data can be represented by a likelihood function, such as the log likelihood function as in Equation (2):

$$L = \sum_{m=1}^{M} \log p(g(y^m; \psi^m) | X^m, \theta) - \log \frac{\partial g(y^m; \psi^m)}{\partial y^m}$$

where $g(y^m; \psi^m)$ represent the mapping functions 110 used to map each measurement group 104 to the shared latent space 116. In order to ensure that the mapping of each measurement group 104 to the shared latent space 116 preserves the ordering of observation pairs of input and output data, the mapping functions 110 for each measurement group 104 can be defined as in Equation (3):

$$g(y^m; \psi^m) = d \cdot y^m + \sum_{t=1}^{T} a_t \cdot \tanh(b_t \cdot (y^m + c_t))$$

where T represents a number of hyperbolic tangent basis functions, $\psi^m \equiv \{a,b,c,d\}$ and where $a_t \geq 0$, $b_t \geq 0$, and $d_t \geq 0$. Point estimates for transformation parameters $\{\psi^m\}$ and model parameters $\theta$ can then be inferred using gradient descent to map different measurement groups to a shared latent space.

Because each basis function is monotonic, and because monotonic functions are closed under addition, the mapping of each measurement group 104 to the shared latent space 116 remains monotonic. Stated differently, the mapping of each measurement group to the shared latent space 116 preserves an ordering of input data and output data observation pairs of each measurement group when mapped to the shared latent space, independent of a unit of measurement associated with each measurement group.

After jointly inferring both the mapping functions and model parameters for the predictive model using optimization or inference (e.g., maximum likelihood and so on), new input data can be applied to the learned mapping functions to generate predicted outputs from the new input data. Represented mathematically, a predictive distribution for a given test point '*' can be derived from the predictive distribution $p(y_*^m | x_*, \hat{\theta}, \hat{\psi})$. This predictive distribution enables derivation of a test point's expected or predicted value, which is useable to determine predicted outputs from new input data applied to the predictive distribution.

Thus, the techniques described herein enable predicting an output value based on an input value using knowledge or intelligence garnered from training data of input data and output data, by mapping supervised target variables of the output training data that were obtained using various measurement technologies, to a shared latent space.

Figure 2:
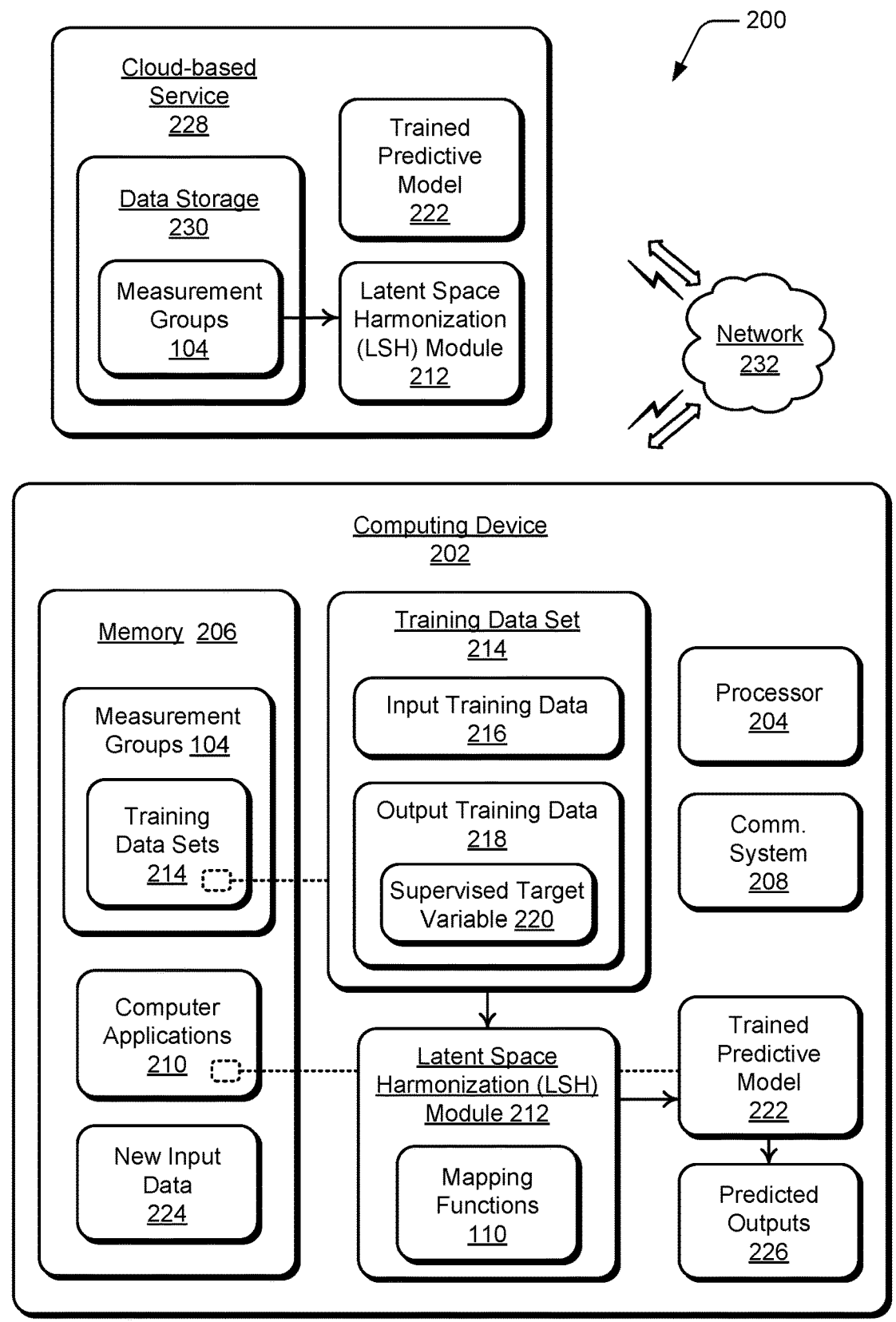
FIG. 2 illustrates an example system in which embodiments of latent space harmonization for predictive modeling can be implemented.

FIG. 2 illustrates an example system 200 in which embodiments of latent space harmonization for predictive modeling can be implemented. The example system 200 includes a computing device 202, such as a computer device that maps the measurement groups 104 to the shared latent space 116 using the techniques shown and described with reference to FIG. 1. The computing device 202 can be implemented with various components, such as a processor 204 (or processing system) and memory 206, with any number and combination of different components as further described with reference to the example device shown in FIG. 4. Although not illustrated, the computing device 202 may be implemented as a mobile or portable device and can include a power source, such as a battery, to power the various device components. Further, the computing device 202 can include different wireless radio systems, such as for Wi-Fi, Bluetooth™, Mobile Broadband, LTE, or any other wireless communication system or format. Generally, the computing device 202 implements a communication system 208 that includes a radio device, antenna, and chipset that is implemented for wireless communication with other devices, networks, and services.

As described herein, the techniques for latent space harmonization for predictive modeling enable mapping of output data that is represented in different measurement spaces into a shared latent space by using the predictive power of input data in a common measurement space across multiple training data groups. The disclosed techniques also include implementation of the trained predictive model to generate predicted outputs based on new input data. The computing device 202 includes one or more computer applications 210, such as the latent space harmonization module 212 to implement latent space harmonization of data from different measurement groups 104 to a shared latent space. In implementations, the measurement groups 104 include at least one training data set 214 and are stored in the device memory 206. Although only one measurement group 104 is illustrated, the device memory 206 is configured to store any number of the measurement groups 104, which each represent different measurement techniques used to observe a physical principle or phenomenon.

Each training data set 214 includes input training data 216 and output training data 218, which represent quantified measurements of a measurement technique of a respective measurement group 104 used to obtain the training data set 214. The output training data 218 includes a supervised target variable 220, which represents a quantifiable value output in a measurement space and obtained from the measurement technique corresponding to the measurement group 104. As described herein, the input training data 216 represents a quantifiable value in a single measurement space across different measurement groups 104. Similarly, the supervised target variable 220 of the output training data 218 remains constant among the training data sets 214 produced from different measurement groups 104. However, the output training data 218 may be represented in different measurement spaces for different training data sets 214, based on different measurement techniques used to obtain the different measurement groups 104.

The latent space harmonization module 212 is implemented to determine and store one or more mapping functions 110 that map the supervised target variables 220 obtained from different measurement techniques to a shared latent space in which data of different training data sets can be jointly yielded, independent of a measurement technique that was used to obtain the training data. After determining the one or more mapping functions 110, the latent space harmonization module 212 generates a trained predictive model 222, which can be stored as one of the computer applications 210, in accordance with one or more implementations. The trained predictive model 222 is designed to receive new input data 224 and generate one or more predicted outputs 226 from the received new input data. In implementations, the new input data 224 is received by the trained predictive model 222 from the memory 206 of the computing device 202. Alternatively or additionally, the new input data 224 may be received from a source that is remote to the computing device 202, such as from a cloud-based service 228 via network 232.

The latent space harmonization module 212 and/or the trained predictive model 222 can each be implemented as a software application or module, such as computer-executable software instructions that are executable with the processor 204 (or with a processing system) to implement embodiments described herein. The latent space harmonization module 212 and the trained predictive model 222 can be stored on computer-readable storage memory (e.g., the device memory 206), such as any suitable memory device or electronic data storage implemented in the computing device. Although shown as separate modules or components, the latent space harmonization module 212 and the trained predictive model 222 may be integrated as a single module, component, or software application.

The example system 200 can include the cloud-based service 228 that is accessible by client devices, to include the computing device 202. The cloud-based service 228 includes data storage 230 that may be implemented as any suitable memory, memory device, or electronic data storage for network-based storage. The data storage 230 can maintain the measurement groups 104 and included training data sets 214. Although not illustrated, the data storage 230 can additionally maintain new input data 224 to be used by the trained predictive model 222 to generate the predicted outputs 226. The cloud-based service 228 can implement an instance of the latent space harmonization module 212 to generate the trained predictive model 222, which can similarly be hosted by the cloud-based service as network-based applications that are accessible by a computer application 210 from the computing device 202.

The cloud-based service 228 can also be implemented with server devices that are representative of one or multiple hardware server devices of the service. Further, the cloud-based service 228 can be implemented with various components, such as a processing system and memory, as well as with any number and combination of different components as further described with reference to the example device shown in FIG. 4 to implement the services, applications, servers, and other features of latent space harmonization to generate predictive models. Aspects of predictive modeling with latent space harmonization as described herein can be implemented by the latent space harmonization module 212 at the cloud-base service and/or may be implemented in conjunction with the latent space harmonization module 212 that is implemented by the computing device 202.

The example system 200 also includes the network 232, and any of the devices, servers, and/or services described herein can communicate via the network, such as for data communication between the computing device 202 and the cloud-based service 228. The network can be implemented to include a wired and/or a wireless network. The network can also be implemented using any type of network topology and/or communication protocol, and can be represented or otherwise implemented as a combination of two or more networks, to include IP-based networks and/or the Internet. The network may also include mobile operator networks that are managed by a mobile network operator and/or other network operators, such as a communication service provider, mobile phone provider, and/or Internet service provider.

In embodiments, the latent space harmonization module 212 receives the training data sets 214 that are obtained using fundamentally different measurement techniques, such that the output training data 218 of one training data set does not correlate to the output training data of another training data set. The latent space harmonization module 212 maps the supervised target variables 220 of the output training data 218 from multiple training data sets to a shared latent space, in which data represented by disparate measurement scales can be jointly yielded, independent of a measurement technique that was used to measure the training data. The mapping functions 110 are generated for each training data set 214 such that the supervised target variable 220 of each training data set can be mapped from the shared latent space. These mapping functions 110 are used by the latent space harmonization module 212 to generate the trained predictive model 222. The trained predictive model 222 can then receive the new input data 224 and generate the predicted outputs 226, thereby eliminating the need for costly and time-consuming measurement procedures otherwise required to determine outputs from the new input data.

Example method 300 is described with reference to FIG. 3 in accordance with one or more embodiments of latent space harmonization for predictive modeling. Generally, any of the components, modules, methods, and operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternatively or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like.

Figure 3:
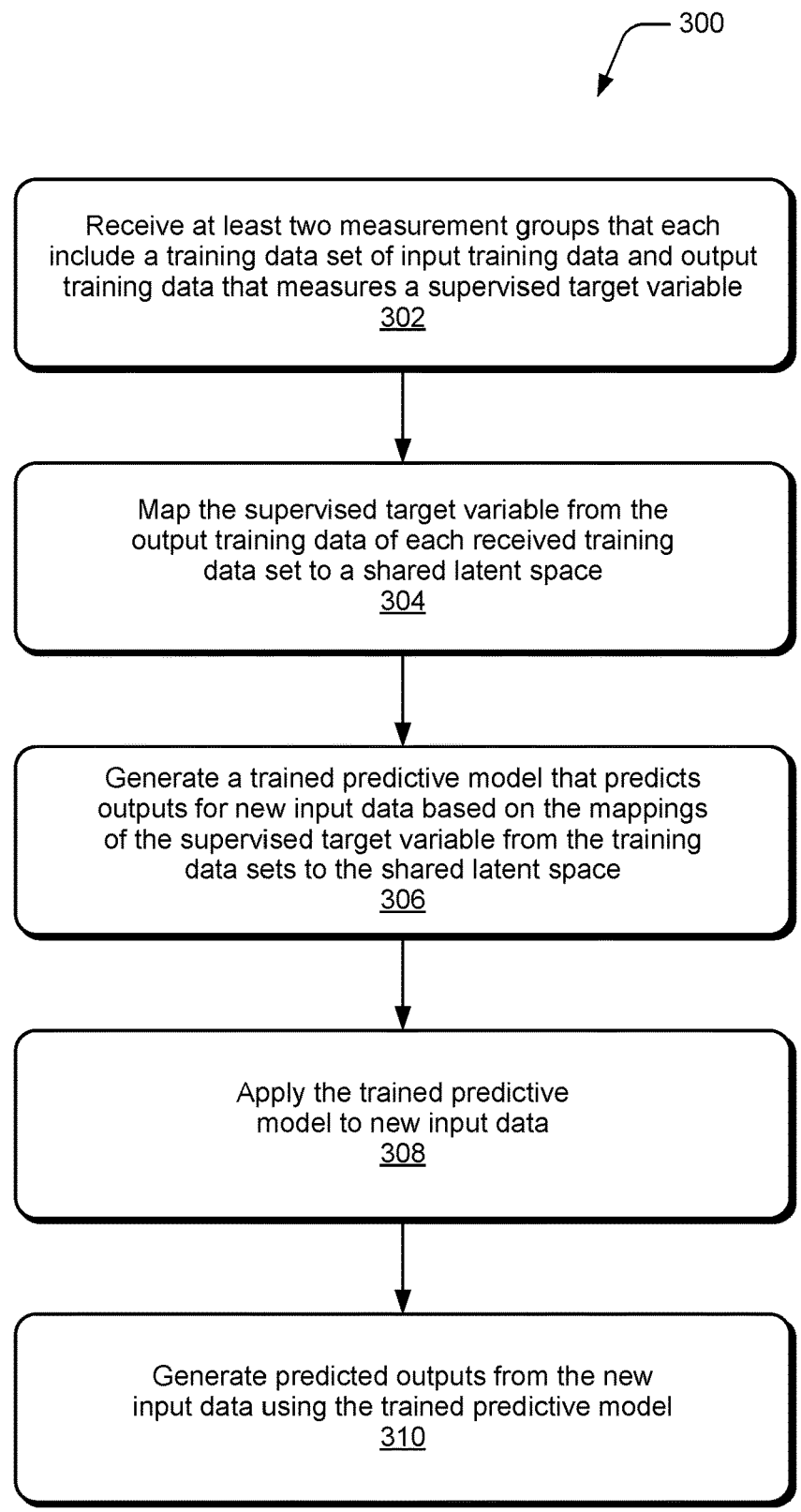
FIG. 3 illustrates example method(s) of latent space harmonization for predictive modeling in accordance with one or more embodiments.

FIG. 3 illustrates an example method 300 of generating predictive models using the latent space harmonization techniques discussed herein, and is generally described with reference to FIGS. 1 and 2. The order in which the method is described is not intended to be construed as a limitation, and any number or combination of the method operations can be performed in any order to implement a method, or an alternate method.

At 302, at least two measurement groups are received, where each measurement group includes a training data set of input training data and output training date that measures a supervised target variable, such as for a physical principle or phenomenon. For example, the latent space harmonization module 212 receives two or more of the measurement groups 104 that each include at least one training data set 214. Each measurement group 104 represents data obtained by a single measurement technique used to observe the physical principle or phenomenon. Each training data set 214 includes the input training data 216 and the output training data 218, which represents a measurement pertaining to the supervised target variable 220. The input training data 216 of the two measurement groups 104 are quantified in a common measurement space, such as a common or comparable unit of measurement.

However, because each of the measurement groups 104 correspond to a different measurement technique, the output training data 218 of each measurement group is quantified in a unique measurement space that is not comparable to the measurement space of different output training data. Although the supervised target variable 220 is represented in different measurement spaces, it represents a measurement of a common aspect of a physical principle or phenomenon. For example, in implementations where one of the measurement groups 104 includes training data sets obtained using flow cytometry and a different one of the measurement groups includes training data sets obtained using drug resistance assay, the different measurement groups share the common supervised target variable 220 of the efficiency of gene knock out based on an input DNA sequence. This common supervised target variable 220, although represented in disparate measurement spaces, can be mapped to a shared latent space.

At 304, the supervised target variables from the output training data of each received training data set is mapped to a shared latent space. For example, a mapping function 110 is determined for the training data sets 214 generated from an individual measurement group 104, which maps the supervised target variable 220 of each training data set back to the shared latent space. Because a different mapping function 110 is generated for each training data set 214 based on a measurement technique that was used to obtain data of the training data set, the shared latent space unifies different measurement spaces that define the respective supervised target variables 220. Thus, the shared latent space provides a cohesive set of data that enables data from disparate measurement groups 104 to be jointly yielded.

At 306, a trained predictive model is generated, which predicts outputs for new input data based on the mappings of the supervised target variable from the training data sets to the shared latent space. For example, the latent space harmonization module 212 generates the trained predictive model 222 based on the mapping functions 110 that were used to map data of the training data sets 214 to a shared latent space.

At 308, new input data is applied to the trained predictive model. For example, the new input data 224 is input to the trained predictive model 222. Further, at 310, predicted outputs from the new input data are generated using the trained predictive model. For example, the trained predictive model 222 generates one or more predicted outputs 226 from the new input data 224. In implementations, these predicted outputs 226 are probabilistically determined based on the inferred mapping of the supervised target variables from different measurement groups to a shared latent space. Thus, the trained predictive model 222 is implemented to predict outputs 226 for the new input data 224 without the need for expensive testing procedures.

Figure 4:
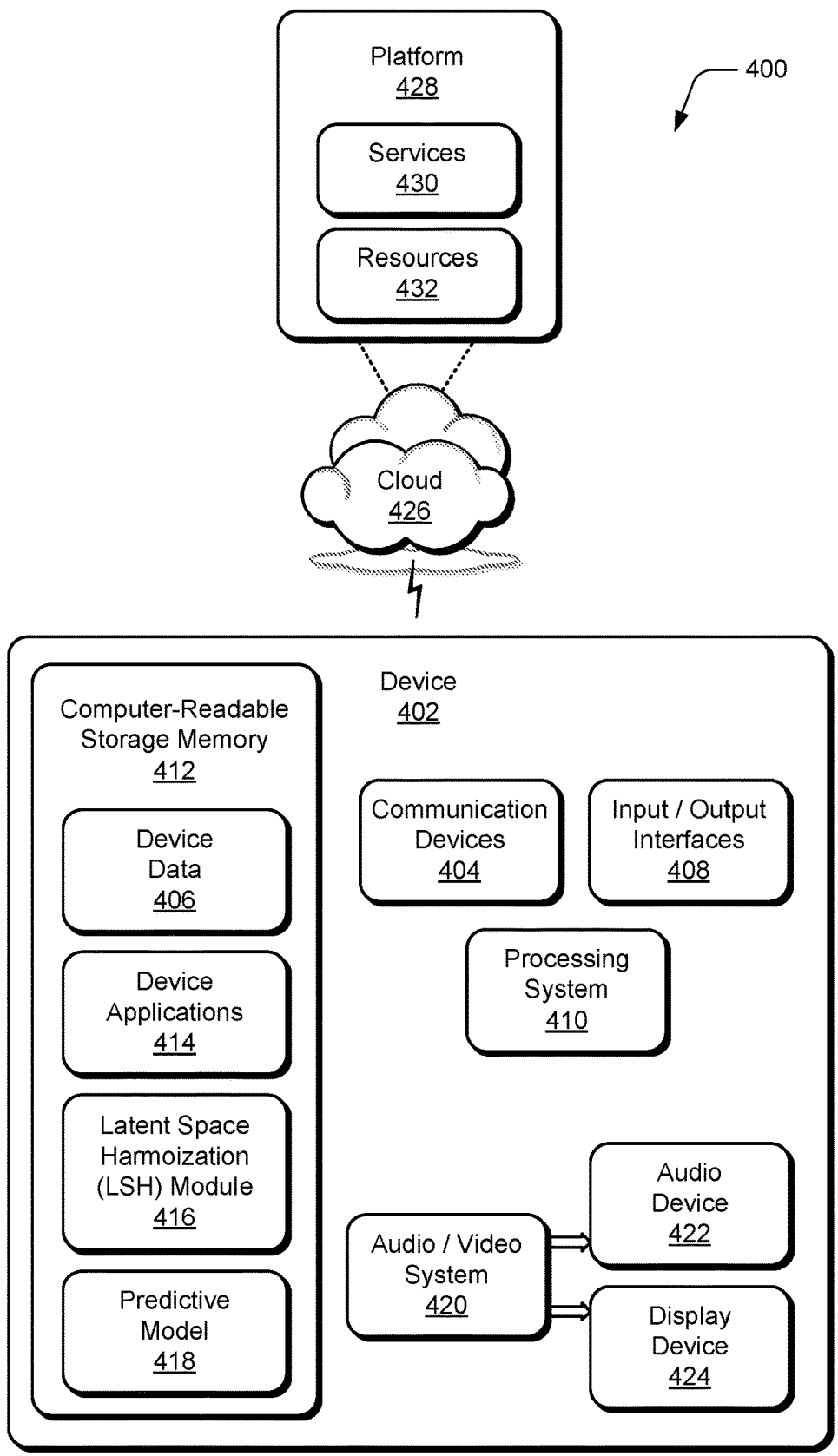
FIG. 4 illustrates an example system with an example device that can implement embodiments of latent space harmonization for predictive modeling.

FIG. 4 illustrates an example system 400 that includes an example device 402, which can implement latent space harmonization for predictive modeling using the techniques described herein. The example device 402 can be implemented as any of the computing devices, user devices, and server devices described with reference to the previous FIGS. 1-3, such as any type of mobile device, client device, mobile phone, tablet, computing, communication, entertainment, gaming, media playback, and/or other type of device. For example, the computing device 202 and the cloud-based service 228 described herein may be implemented as the example device 402 or with various components of the example device.

The device 402 includes communication devices 404 that enable wired and/or wireless communication of device data 406, such as training data useable to train one or more predictive models, and new input data that can be input to a trained predictive model to produce predicted outputs. Additionally, the device data 406 can include any type of audio, video, and/or image data. The communication devices 404 can also include transceivers for cellular phone communication and for network data communication.

The device 402 also includes input/output (I/O) interfaces 408, such as data network interfaces that provide connection and/or communication links between the device, data networks, and other devices described herein. The I/O interfaces can be used to couple the device to any type of components, peripherals, and/or accessory devices. For example, the I/O interfaces can be used to couple the device to measurement instruments that are useable to measure and record training data sets for training a predictive model using the techniques described herein. The I/O interfaces also include data input ports via which any type of data, media content, and/or inputs can be received, such as user inputs to the device, as well as any type of audio, video, and/or image data received from any content and/or data source.

The device 402 includes a processing system 410 that may be implemented at least partially in hardware, such as with any type of microprocessors, controllers, and the like that process executable instructions. The processing system can include components of an integrated circuit, programmable logic device, a logic device formed using one or more semiconductors, and other implementations in silicon and/or hardware, such as a processor and memory system implemented as a system-on-chip (SoC). Alternatively or in addition, the device can be implemented with any one or combination of software, hardware, firmware, or fixed logic circuitry that may be implemented with processing and control circuits. The device 402 may further include any type of a system bus or other data and command transfer system that couples the various components within the device. A system bus can include any one or combination of different bus structures and architectures, as well as control and data lines.

The device 402 also includes a computer-readable storage memory 412, such as data storage devices that can be accessed by a computing device, and that provide persistent storage of data and executable instructions (e.g., software applications, programs, functions, and the like). Examples of the computer-readable storage memory 412 include volatile memory and non-volatile memory, fixed and removable media devices, and any suitable memory device or electronic data storage that maintains data for computing device access. The computer-readable storage memory can include various implementations of random access memory (RAM) (e.g., the DRAM and battery-backed RAM), read-only memory (ROM), flash memory, and other types of storage media in various memory device configurations.

The computer-readable storage memory 412 provides storage of the device data 406 and various device applications 414, such as an operating system that is maintained as a software application with the computer-readable storage memory and executed by the processing system 410. In this example, the device applications include a latent space harmonization module 416 that implements embodiments of the latent space harmonization techniques described herein with reference to FIGS. 1-3, and is useable to generate one or more predictive models 418, which are also stored in the computer-readable storage memory 412. An example implementation of the latent space harmonization module 416 is the latent space harmonization module 212 that is shown and described with reference to FIG. 2.

The device 402 also includes an audio and/or video system 420 that generates audio data for an audio device 422 and/or generates display data for a display device 424. The audio device and/or the display device include any devices that process, display, and/or otherwise render audio, video, display, and/or image data. In implementations, the audio device and/or the display device are integrated components of the example device 402. Alternatively, the audio device and/or the display device are external, peripheral components to the example device.

In embodiments, at least part of the latent space harmonization for predictive modeling techniques may be implemented in a distributed system, such as over a "cloud" 426 in a platform 428. The cloud 426 includes and/or is representative of the platform 428 for services 430 and/or resources 432. The platform 428 abstracts underlying functionality of hardware, such as server devices (e.g., included in the services 430) and/or software resources (e.g., included as the resources 432), and connects the example device 402 with other devices, servers, etc. The resources 432 may also include applications and/or data that can be utilized while computer processing is executed on servers that are remote from the example device 402. Additionally, the services 430 and/or the resources 432 may facilitate subscriber network services, such as over the Internet, a cellular network, or Wi-Fi network. The platform 428 may also serve to abstract and scale resources to service a demand for the resources 432 that are implemented via the platform, such as in an interconnected device embodiment with functionality distributed throughout the system 400. For example, the functionality may be implemented in part at the example device 402 as well as via the platform 428 that abstracts the functionality of the cloud.

Although embodiments of latent space harmonization for predictive modeling have been described in language specific to features and/or methods, the appended claims are not necessarily limited to the specific features or methods described. Rather, the specific features and methods are disclosed as example implementations of latent space harmonization for predictive modeling, and other equivalent features and methods are intended to be within the scope of the appended claims. Further, various different embodiments are described and it is to be appreciated that each described embodiment can be implemented independently or in connection with one or more other described embodiments. Additional aspects of the techniques, features, and/or methods discussed herein relate to one or more of the following embodiments.

A computing system implemented for predictive modeling, the system comprising: memory configured to maintain different measurement groups each including training data sets of input training data and output training data for use in predictive modeling of a physical principle or phenomenon; a processor system to implement a latent space harmonization module, the latent space harmonization module configured to: receive the training data sets of the input training data and the output training data from two or more of the measurement groups, the output data of the two or more measurement groups including a supervised target variable of the physical principle or phenomenon; generate a mapping function for each of the two or more measurement groups, the mapping function for a measurement group mapping the supervised target variable for the measurement group to a shared latent space; and train a predictive model that is configured to predict outputs for new input data based on the mappings of the supervised target variable of each of the two or more measurement groups to the shared latent space.

Alternatively or in addition to the above described computing system, any one or combination of: the latent space harmonization module is configured to: apply new input data to the trained predictive model; and generate predicted outputs from the applied new input data using the trained predictive model. The input training data for the two or more measurement groups shares a common measurement scale. The training data sets of each of the two or more measurement groups comprise training data obtained using different measurement techniques. The supervised target variable comprises a quantifiable value in an output measurement space that is obtained from observing a response of the physical principle or phenomenon to input data. The shared latent space comprises a single coherent data set that is mappable to supervised target variables included in each of the two or more measurement groups. The mapping function for each of the two or more measurement groups is a monotonic transformation that preserves or reverses an order of data in each of the two or more measurement groups. The physical principle or phenomenon is a correlation between protein abundance and a messenger ribonucleic acid (mRNA) sequence. The physical principle or phenomenon is a correlation between a deoxyribonucleic acid (DNA) sequence and an efficiency in disabling functionality of a gene in a genome. The input training data comprises a 30-letter DNA sequence; and the output training data comprises a measured efficiency in disabling functionality of the gene in the genome. One of the two or more measurement groups comprises training data generated from a flow cytometry process and another one of the two or more measurement groups comprises training data generated from a drug resistance assay process.

A method comprising: receiving training data that was obtained using at least two different measurement techniques, the training data obtained from each different measurement technique including input training data and output training data that is representative of a physical principle or phenomenon; generating a mapping function using the training data obtained from each different measurement group, the mapping function for a measurement group mapping a supervised target variable generated as an output of the measurement group to a shared latent space that unifies data represented in disparate measurement scales; and training a predictive model from the mapping functions and the received training data, the predictive model configured to predict output values from new input data.

Alternatively or in addition to the above described method, any one or combination of: the method further comprising applying the new input data to the trained predictive model; and generating predicted outputs for the new input data. The mapping function for each measurement group is a monotonic transformation that preserves or reverses an order of data in the measurement group. The supervised target variable comprises a quantifiable value in an output measurement space that is obtained from observing a response of the physical principle or phenomenon to input data. The shared latent space comprises a single coherent data set that is mappable to the supervised target variables obtained from each different measurement technique. The mapping function between each different measurement technique and the shared latent space is a mathematically inferred relationship between all input training data and all output training data included in the different measurement techniques. The at least two different measurement techniques comprise a flow cytometry technique and a drug resistance assay technique; and the supervised target variable comprises a measure of efficiency in disabling functionality of a gene in the human genome.

A computer-readable storage memory comprising stored instructions that are executable and, responsive to execution of the stored instructions by a computing system, the computing system performs operations comprising: receiving data that is represented in at least two different measurement scales, the received data including input data and output data for each of the different measurement scales; determining a mapping function for each of the different measurement scales that is configured to map data represented in the measurement scale to a shared latent space that unifies data represented among the different measurement scales; training a predictive model, based on the determined mapping functions, that is configured to predict outputs for new input data; and generating predicted outputs by applying new input data to the trained predictive model.

The invention claimed is:

1. A computing system to train a predictive model that models a physical principle or phenomenon using two or more training data sets including respective incomparable units of measurement, the system comprising:
    memory configured to maintain different measurement groups each including training data sets of input training data and output training data;
    a processor system configured to:
    receive the training data sets of the input training data and the output training data from two or more of the measurement groups, the output data of the two or more measurement groups including supervised target variables of the physical principle or phenomenon;
    generate respective monotonic mapping functions for each of the two or more measurement groups to map output training data for each of the two or more measurement groups to a shared latent space by inferring monotonic relationships between the output training data for each of the two or more measurement groups and the shared latent space based on the input training data and the supervised target variables;
    generate, using the monotonic mapping function for each of the two or more measurement groups, a combined training data set that maps the input training data from the two or more measurement groups to corresponding output training data in the shared latent space, such that the combined training data set includes a larger number of data samples than any of the training data sets from the two or more measurement groups, by transforming output training data from the two or more of the measurement groups to the output training data in the shared latent space; and
    train a model that predicts outputs for new input data using machine learning and the combined training data set.

2. The computing system as recited in claim 1, wherein the processor system is configured to:
    transform output data generated by the trained predictive model in the shared latent space to output data in a measurement scale of at least one measurement group of the two or more measurement groups.

3. The computing system as recited in claim 1, wherein the input training data for the two or more measurement groups shares a common measurement scale.

4. The computing system as recited in claim 1, wherein the output training data for one of the two or more measurement groups is quantified in a measurement scale that is different from the output training data for another one of the two or more measurement groups.

5. The computing system as recited in claim 1, wherein the training data sets of each of the two or more measurement groups comprise training data obtained using different measurement techniques.

6. The computing system as recited in claim 5, wherein the output training data in the shared latent space comprises a single data set that is mappable to supervised target variables included in each of the two or more measurement groups, and pairs of input data and output data in the shared latent space preserves an ordering of corresponding pairs of input training data and output training data in the training data sets.

7. The computing system as recited in claim 1, wherein the physical principle or phenomenon is a correlation between protein abundance and a messenger ribonucleic acid (mRNA) sequence.

8. The computing system as recited in claim 1, wherein the physical principle or phenomenon is a correlation between a deoxyribonucleic acid (DNA) sequence and an efficiency in disabling functionality of a gene in a genome.

9. The computing system as recited in claim 8, wherein:
    the input training data comprises a 30-letter DNA sequence; and
    the output training data comprises a measured efficiency in disabling functionality of the gene in the genome.

10. The computing system as recited in claim 8, wherein one of the two or more measurement groups comprises training data generated from a flow cytometry process and another one of the two or more measurement groups comprises training data generated from a drug resistance assay process.

11. A method comprising:
    receiving training data that was obtained using at least two different measurement techniques, the training data obtained from each different measurement technique including input training data and output training data that is representative of a physical principle or phenomenon;
    generating respective monotonic mapping functions using the training data obtained from each of the different measurement techniques to map output training data for each of the different measurement techniques to a shared latent space by inferring monotonic relationships between the output training data for each of the two or more measurement groups and the shared latent space based on the input training data and supervised target variables, wherein the shared latent space unifies data represented in measurement spaces that include respective incomparable units of measurement such that unified data in the shared latent space preserves an ordering corresponding data represented in the measurement spaces; and
    generate, using the monotonic mapping function for each of the different measurement techniques, a combined training data set that maps the input training data from the different measurement techniques to corresponding output training data in the shared latent space such that the combined training data set includes a larger number of data samples than any of the training data sets from the different measurement techniques by transforming output training data from the different measurement techniques to the output training data in the shared latent space; and
    training a predictive model using using machine learning and the combined training data set.

12. The method as recited in claim 11, further comprising:
    applying new input data to the trained predictive model; and
    generating predicted outputs for the new input data.

13. The method as recited in claim 11, wherein the output training data in the shared latent space comprises a single data set that is mappable to the supervised target variables obtained from each different measurement technique, and pairs of input data and output data output training data in the shared latent space preserves an ordering of corresponding pairs of input data and output data in the receiving training data.

14. The method as recited in claim 11, wherein:

the at least two different measurement techniques comprise a flow cytometry technique and a drug resistance assay technique; and the supervised target variable comprises a measure of efficiency in disabling functionality of a gene in the human genome.

15. A non-transitory computer-readable storage memory comprising stored instructions that are executable and, responsive to execution of the stored instructions by a computing system, the computing system performs operations for training a predictive model using data from data sets with respective incomparable units of measurement, the operations comprising:

obtaining a first training set comprising input data obtained in a first measurement space and output data obtained in a second measurement space, and obtaining a second training set comprising input data obtained in the first measurement space and output data obtained in a third measurement space, wherein output data obtained in the second measurement space does not have a known mathematical relationship to output data obtained in the third measurement space, transforming the first training set and the second training set into a third training set having a larger number of data samples than each of the first training set and the second training set and output data in a shared latent space by using the first training set and the second training set to infer respective monotonic relationships between the shared latent space and each of the first training set and the second training set and using the inferred monotonic relationships to transform output data of the first training set and the second training set into the output data in the shared latent space, training the predictive model using the third training set.

* * * * *